(12) United States Patent
Gao et al.

(10) Patent No.: US 12,612,640 B2
(45) Date of Patent: Apr. 28, 2026

(54) GENE RELATED TO BIOSYNTHESIS OF ERGOTHIONEINE, AND USE THEREOF

(71) Applicant: Shanghai Academy of Agricultural Sciences, Shanghai (CN)

(72) Inventors: Jianjie Gao, Shanghai (CN); Yongdong Deng, Shanghai (CN); Quanhong Yao, Shanghai (CN); Rihe Peng, Shanghai (CN); Yongsheng Tian, Shanghai (CN); Bo Wang, Shanghai (CN); Zhenjun Li, Shanghai (CN); Jing Xu, Shanghai (CN); Hongjuan Han, Shanghai (CN); Lijuan Wang, Shanghai (CN); Xiaoyan Fu, Shanghai (CN); Yu Wang, Shanghai (CN); Wenhui Zhang, Shanghai (CN); Zhihao Zuo, Shanghai (CN); Cen Qian, Shanghai (CN)

(73) Assignee: Shanghai Academy of Agricultural Sciences, Shanghai (CN)

( * ) Notice: Subject to any disclaimer, the term of this patent is extended or adjusted under 35 U.S.C. 154(b) by 0 days.

(21) Appl. No.: 18/772,908

(22) Filed: Jul. 15, 2024

(65) Prior Publication Data

US 2025/0059553 A1     Feb. 20, 2025

(30) Foreign Application Priority Data

Aug. 17, 2023   (CN) .......................... 202311036218.8

(51) Int. Cl.
| | |
|---|---|
| *C12N 15/82* | (2006.01) |
| *C12N 9/00* | (2006.01) |
| *C12N 9/02* | (2006.01) |
| *C12N 9/10* | (2006.01) |
| *C12N 9/80* | (2006.01) |
| *C12N 9/88* | (2006.01) |
| *C12N 15/52* | (2006.01) |

(52) U.S. Cl.
CPC ....... *C12N 15/8251* (2013.01); *C12N 9/0083* (2013.01); *C12N 9/1007* (2013.01); *C12N 9/80* (2013.01); *C12N 9/88* (2013.01); *C12N 9/93* (2013.01); *C12N 15/52* (2013.01); *C12N 15/8205* (2013.01); *C12N 15/8234* (2013.01); *C12Y 201/01044* (2013.01); *C12Y 603/02002* (2013.01)

(58) Field of Classification Search
None
See application file for complete search history.

(56) References Cited

FOREIGN PATENT DOCUMENTS

CN        104854245 A  *  8/2015  ........... C07D 233/42

OTHER PUBLICATIONS

Applicant Has No Information to Disclose: No patent novelty search was performed in this case and neither the Applicant nor the undersigned are aware of any prior art devices or documents which they believe to be material to the invention as claimed. This document is being supplied for informational purposes to the Examiner and is evidence of our desire to comply with the duty of disclosure.

* cited by examiner

*Primary Examiner* — Charles Logsdon
*Assistant Examiner* — Jessica Nicole Stockdale
(74) *Attorney, Agent, or Firm* — Daniel A. Thomson; Emerson, Thomson & Bennett, LLC

(57) ABSTRACT

A gene related to biosynthesis of ergothioneine is provided. Based on five synthesis genes of ergothioneine in *Mycobacteroides abscessus*, only an encoding sequence of each of the five genes is retained, and a gene structure of an encoding region in each gene is optimized to obtain genes related to the biosynthesis of the ergothioneine that are stably expressed in rice. These genes have sequences set forth in SEQ ID NO: 1 to SEQ ID NO: 5, and encoded proteins thereof have amino acid sequences set forth in SEQ ID NO: 6 to SEQ ID NO: 10. The gene is transferred into rice to construct a transgenic rice molecular farm to produce the ergothioneine. As a molecular farm, rice seeds do not contain alkaloids or allergens that are harmful to the human body. Moreover, biosynthesized ergothioneine shows the advantages of easy extraction and processing and of low production cost.

15 Claims, 5 Drawing Sheets

Specification includes a Sequence Listing.

SEQUENCE LISTING

```
Sequence total quantity: 20
SEQ ID NO: 1            moltype = DNA  length = 1251
FEATURE                 Location/Qualifiers
misc_feature            1..1251
                        note = Optimized nucleotide sequence of the EgtA gene
source                  1..1251
                        mol_type = other DNA
                        organism = synthetic construct
SEQUENCE: 1
atggcaacta ctgcaactga ggctgatact ggtcgtactc tgtctggtca cgatgaagct  60
gctgagcaca tcgcacgtca agcattcgct gatgcacagg ttggtgctgt tggtctggag  120
ctggagtctc acactgtcga gctgactgca ccacaccgtc gtatcacctg gaaccgtctt  180
cgtgaggttg gtgactctgt tcctgatctg cctggttcct ctgccatcac cttcgaacct  240
ggtggtgctg ttgagctgtc tggaccacca cgttctgatg tgtggtctgc catctcatcc  300
atgcgtgctg accatgagat cctgactgct gcataccgtg gtgctggaat cgcactggca  360
tcactgggaa ctgatccact gcgtcgtcct gaacgtgtga atcctggtgc acgttacgtt  420
gcaatggagc gtcacttcgg tgctgctgga tacggtgaga ctgcactcca gatgatgacc  480
tgcactgcct cactccaggt gaacgtgcag tctggaactc cacgtcagtg gcgtgaccgt  540
ttcgttctga cacaacgtat cggaccaact atggctgcac tgtctgcatc ctcaccaatg  600
ctcactggac gtcgtactgg acgtcgtaac actcgtcagt ggatctggga caacttggac  660
ccacgtcgtt gtgcacctgt tgagatcggt gttgatccta ccgagtcatg ggttgagtac  720
gcacttcgtg cacctgtgat gttggttcgt aacaaggatg gtgctgacgc tgttgtcact  780
cacgttcctt tccagtcctg ggttgatgga actatgccac ttgctggacg tgcaccaact  840
actgaggacc tggactacca tctgactacc ttgttcccac ctgttcgtcc acgtcgttgg  900
ttggaactgc gttacctgga tgctgcacct gactggtggt ggcctgcact ggcattcact  960
gctgttgctg cactggatga cccacaggtt gctgatgctg ctgctgagat cgttgagcct  1020
gttggcaacg catggggtgt tgctgcacgt atcggactgg aggaccctgc actgcacgct  1080
gctgcacacc gtctggtgtc tgctgcatgt gctgttgcac cacctgagtt ggctaccgac  1140
atggagttct tgctggaacg tgttgagcaa ggacgttgtc ctgctgacga cttcatcgac  1200
aacgttgctg agtacggtgt tgagaaggca ttctctggtg caatgggata a           1251

SEQ ID NO: 2            moltype = DNA  length = 1284
FEATURE                 Location/Qualifiers
misc_feature            1..1284
                        note = Optimized nucleotide sequence of the EgtB gene
source                  1..1284
                        mol_type = other DNA
                        organism = synthetic construct
SEQUENCE: 2
atgtcacgtg atgagttggc acgtgacctt gaggctgcac gtatgcgtac tctgaccatc  60
actgaccacg atgacgctga actccaccgt cagtacgatc cactgatgtc accactggtc  120
tgggatctgg cacacattgg acagcaagaa gagctgtggc tgctgcgtgg tggtgatcca  180
cgtcgtcctg gaatgctgcc tggtgagatc gagtcactgt atgatgcctt ccgtcacact  240
cgtgcatcac gtgtgcagct tccactgttg tcacctgcac aggcacgtgc attctgtcat  300
gaggttcgtg gtcgtgtctt ggatcgtctt gaggcactgc atctgatgg atctgcacgt  360
gctgaagagt tcgtctatgc aatggttctg tcacatgaac accagcatga cgagactatg  420
atgcaggcac tgtccatccg tcatggtgct gcactgctgg aggctgttga tcctgttcca  480
cctggacgtc ctggtgttgc tggaacctct gtgctggttc ctgagggacc attcgttctg  540
ggtgttgacg ctgttgacga accattctca ctggacaacg aacgtcctgc acatgttgtg  600
catctccgtg gtttccgtat cggaactgtt cctgtgacca acgctgagtg gttggcattc  660
atggcagatg gtggataccg tcgtcaggaa ctctggactg agatcggatg ggcacatcgt  720
tgtgctgaag cactgactgc acctaagttc tggaaccaag gtggaaccct gactcgtttc  780
ggacgtgaac tccagatcgt tcctgacgaa cctgttcaac atgtgacctt ccatgaggca  840
caggcatacg catcatgggc aggtgcacgt ctgccaactg aggctgagtg ggagaaggca  900
tgtgtctggg accctgagat cggtgcacgt cgtcgtttcc cttggggtgc tgaagcacct  960
gcacgtgacc gtgccaatct tggtggtggt gcacttggac ctgcacctgt tggagcatac  1020
cctgagtctg catctgcata cggtgctgaa cagatgcttg tgatgtgtg ggagtggact  1080
acttcacctc tgcgtccttg gcctggattc actcctatga tctaccagca gtactctgaa  1140
ccattcttcg acggtgacta tcgtgttctg cgtggtggat catgggctgt tgcacgtgag  1200
atcatgcgtc catcattccg taactgggat catcctgttc gtcgtcaaat cttctctgga  1260
cttcgtctgg catgggacat ctaa                                          1284

SEQ ID NO: 3            moltype = DNA  length = 681
```

```
FEATURE               Location/Qualifiers
misc_feature          1..681
                      note = Optimized nucleotide sequence of the EgtC gene
source                1..681
                      mol_type = other DNA
                      organism = synthetic construct
SEQUENCE: 3
atgtgtcgtc atcttggatg gcttggtgca ccacgttcac tgtcatcact gatgcttgaa   60
ccaccacatg gtctcgtcgt ccagtcatac tcaccacgtc gtcagaagca tggactggtc  120
aacgctgatg gatggggtgc tggtttcttc gctgacagtg catcacgtcg ttggcgttct  180
gcacgtccac tgtgggtga tgcatccttc gcatctgttg cacctgttct gcgttctgga  240
tgtgttgttg ctgctgttcg ttctgcctct gttggaatgc ctatcgagga aactgctgct  300
gcaccattca ctgatggaac ctggctgctg tcacacaacg gtatcgttga tcgtggtgct  360
gttggtgagg cattcggtgc tgagtctgtt gttgactctg caatccttgc tgcacgtatc  420
ttcgcatctg gtgtgcagaa tcttggtgaa actgttcgtc agattggtgc tgctgatcct  480
ggtgcacgtc tgaacatcct ggctgccaac ggtaacgagt tggttgcaac cacttggggt  540
gataccctgt ccatcctgga agctgctgat ggtgttgtgt ttgcttctga accatacgat  600
gatgatccat catgggttga cattcctgat cgtcgtctgg ttcgtgtgcg tgatggtaag  660
gtggagatcg aaggtctgta a                                            681

SEQ ID NO: 4             moltype = DNA  length = 969
FEATURE               Location/Qualifiers
misc_feature          1..969
                      note = Optimized nucleotide sequence of the EgtD gene
source                1..969
                      mol_type = other DNA
                      organism = synthetic construct
SEQUENCE: 4
atgactccat tgccaccaat gactcttgag aatcatctgg catctggtgc agcagcagca   60
gcacttcgtc gtgacgttcg tcagggtctg actgccaagg ccaagtcact tccacctaag  120
tggttctacg acgaggctgg ttctgatctg ttcgacgaga tcactcgtct tcctgagtac  180
tatccaactc gtactgaggc aggactgctt cgtgcacatg ctgctgacat cgctgctgca  240
tgtggtgctg acactctggt tgagcttgga tctggaacct ctgagaagac tcgtatgctg  300
ctggatgcac tcgatcctaa caccttcatc ccattcgatg ttgactctgg tgtcctgcgt  360
gcagcaggtg atgcactggt tgctgagtac cctggaatgt ctgttcgtgc tgtctgtgga  420
gacttcgaga aggatcttgc acgtatccca cgtgagggac gtcgtctggt tgccttcctt  480
ggatctacca tcggtaatct gactgctgaa ccacgtgcac gtttcctggc tgatgttgct  540
gcaactctgc aatctggtga gatgctgctg ttgggaaccg acttggtcaa ggatgctgag  600
cgtctggttc gtgcctacga cgactctgct ggtgttactg ctgcattcaa ccgtaacgtt  660
ctggctgtca tcaatcgtga actggatgct gacttcgatc tggatgcatt cgatcatgtt  720
gcacgttgga atggtgatga agaacgtatg gagatgtggt tgcgttctgt tcgtgatcag  780
cgtatcacta tcgaagcact ggatctgtct gttgacttcg aagctggtga gatgatgctg  840
actgaggtct catgcaagtt ccgtcgtgaa ggtgttgcac gtgaacttgc tgctgctgga  900
ctgcgtcaga ctcactggtg gactgacgat gctgacgact tcggactgtc acttgctgtc  960
aaggagtaa                                                          969

SEQ ID NO: 5             moltype = DNA  length = 1083
FEATURE               Location/Qualifiers
misc_feature          1..1083
                      note = Optimized nucleotide sequence of the EgtE gene
source                1..1083
                      mol_type = other DNA
                      organism = synthetic construct
SEQUENCE: 5
atgtcactgc gtgatcgttg gcgtcaagca cgtccacctg ttcttggtgt tcaccttgac   60
tctgctgcat gttcacgtca gtctgttgag actcttcgtg ctgttgctca acatgctgaa  120
catgaagcac agatcggtgg ctacgttgca caagaagctg ctactcctgt tcttgaggct  180
ggacgtgctg ctgttcgtca gctgactggt atgcctgagg cacatgttca gttcaccact  240
ggtgctgctg atgcactgcg tactctgttg caggcatggc ctgctgatgg aggacgtgtc  300
atcgcatgtc ttcctgatga gttcggacct aacctgatga tcatgaacca cttcggcttc  360
actcctgtgt ggcttcctgt tgatggtgat ggacgtgctg atgctgatgg catcgaggtc  420
ttccttcgtc acgagaagat cgatctgctg cacctgactg ttgttggatc acatcgtgga  480
actgttcagc ctgctgctga ggttgttgca cttcacgtg ctgctggtgt tcctgtcgtc  540
gtcgatgctg cacaggcact tggacacatc gactgcacct acggtgctga ggccatgtac  600
gcaccttcac gtaagtggtt ggctggacca cgtggtgtcg gtgttcttgc tgtcaaccct  660
gttcttgagt acctgctgcc acagtgggct ggacatgttg aggcacacgt tgctggatgg  720
gttggactgt ctgttgctgt tggacagcat ctggctgctg gacctgagcg tatccagggt  780
gcactggctg aacgtggacg tgctgcacgt aagatcctgg gtgagttgaa ggactggcgt  840
gtgatcgagt ctgtggatga gccatctgcc atcaccactc ttgagcctgt tggtgacatc  900
gacgtgatcg ctgttcgtgc acgtctgatc gaggagcacg ctatcgtgac tactggtgct  960
gagaccatcc gtgcaccatt cgagatgacc actcctgttc tgcgtgtgtc accacatgtg 1020
gatggaactg atgaggagct ggaactgctt gctggtgcac tggcatctgc acgtcgtgtg 1080
taa                                                               1083

SEQ ID NO: 6             moltype = AA   length = 416
FEATURE               Location/Qualifiers
REGION                1..416
                      note = Amino acid sequence of protein encoded by the
                      optimized EgtA gene
```

-continued

```
source                  1..416
                        mol_type = protein
                        organism = synthetic construct
SEQUENCE: 6
MATTATEADT GRTLSGHDEA AEHIARQAFA DAQVGAVGLE LESHTVELTA PHRRITWNRL   60
REVGDSVPDL PGSSAITFEP GGAVELSGPP RSDVWSAISS MRADHEILTA AYRGAGIALA  120
SLGTDPLRRP ERVNPGARYV AMERHFGAAG YGETALQMMT CTASLQVNVQ SGTPRQWRDR  180
FVLAQRIGPT MAALSASSPM LTGRRTGRRN TRQWIWDNLD PRRCAPVEIG VDPTESWVEY  240
ALRAPVMLVR NKDGADAVVT HVPFQSWVDG TMPLAGRAPT TEDLDYHLTT LFPPVRPRRW  300
LELRYLDAAP DWWWPALAFT AVAALDDPQV ADAAAEIVEP VGNAWGVAAR IGLEDPALHA  360
AAHRLVSAAC AVAPPELATD MEFLLERVEQ GRCPADDFID NVAEYGVEKA FSGAMG      416

SEQ ID NO: 7            moltype = AA  length = 427
FEATURE                 Location/Qualifiers
REGION                  1..427
                        note = Amino acid sequence of protein encoded by the
                         optimized EgtB gene
source                  1..427
                        mol_type = protein
                        organism = synthetic construct
SEQUENCE: 7
MSRDELARDL EAARMRTLTI TDHDDAELHR QYDPLMSPLV WDLAHIGQQE ELWLLRGGDP   60
RRPGMLPGEI ESLYDAFRHT RASRVQLPLL SPAQARAFCH EVRGRVLDRL EALPSDGSAR  120
AEEFVYAMVL SHEHQHDETM MQALSIRHGA ALLEAVDPVP PGRPGVAGTS VLVPEGPFVL  180
GVDAVDEPFS LDNERPAHVV HLRGFRIGTV PVTNAEWLAF MADGGYRRQE LWTEIGWAHR  240
CAEALTAPKF WNQGGTLTRF GRELQIVPDE PVQHVTFHEA QAYASWAGAR LPTEAEWEKA  300
CVWDPEIGAR RRFPWGAEAP ARDRANLGGG ALGPAPVGAY PESASAYGAE QMLGDVWEWT  360
TSPLRPWPGF TPMIYQQYSE PFFDGDYRVL RGGSWAVARE IMRPSFRNWD HPVRRQIFSG  420
LRLAWDI                                                           427

SEQ ID NO: 8            moltype = AA  length = 226
FEATURE                 Location/Qualifiers
REGION                  1..226
                        note = Amino acid sequence of protein encoded by the
                         optimized EgtC gene
source                  1..226
                        mol_type = protein
                        organism = synthetic construct
SEQUENCE: 8
MCRHLGWLGA PRSLSSLMLE PPHGLVVQSY SPRRQKHGLV NADGWGAGFF ADGASRRWRS   60
ARPLWGDASF ASVAPVLRSG CVVAAVRSAS VGMPIEETAA APFTDGTWLL SHNGIVDRGA  120
VGEAFGAESV VDSAILAARI FASGVQNLGE TVRQIGAADP GARLNILAAN GNELVATTWG  180
DTLSILEAAD GVVVASEPYD DDPSWVDIPD RRLVRVRDGK VEIEGL                226

SEQ ID NO: 9            moltype = AA  length = 322
FEATURE                 Location/Qualifiers
REGION                  1..322
                        note = Amino acid sequence of protein encoded by the
                         optimized EgtD gene
source                  1..322
                        mol_type = protein
                        organism = synthetic construct
SEQUENCE: 9
MTPLPPMTLE NHLASGAAAA ALRRDVRQGL TAKAKSLPPK WFYDEAGSDL FDEITRLPEY   60
YPTRTEAGLL RAHAADIAAA CGADTLVELG SGTSEKTRML LDALDPNTFI PFDVDSGVLR  120
AAGDALVAEY PGMSVRAVCG DFEKDLARIP REGRRLVAFL GSTIGNLTAE PRARFLADVA  180
ATLQSGEMLL LGTDLVKDAE RLVRAYDDSA GVTAAFNRNV LAVINRELDA DFDLDAFDHV  240
ARWNGDEERM EMWLRSVRDQ RITIEALDLS VDFEAGEMML TEVSCKFRRE GVARELAAAG  300
LRQTHWWTDD ADDFGLSLAV KE                                           322

SEQ ID NO: 10           moltype = AA  length = 360
FEATURE                 Location/Qualifiers
REGION                  1..360
                        note = Amino acid sequence of protein encoded by the
                         optimized EgtE gene
source                  1..360
                        mol_type = protein
                        organism = synthetic construct
SEQUENCE: 10
MSLRDRWRQA RPPVLGVHLD SAACSRQSVE TLRAVAQHAE HEAQIGGYVA QEAATPVLEA   60
GRAAVRQLTG MPEAHVQFTT GAADALRTLL QAWPADAGRV IACLPGEFGP NLMIMNHFGF  120
TPVWLPVDGD GRADADGIEV FLRHEKIDLL HLTVVGSHRG TVQPAAEVVA LARAAGVPVV  180
VDAAQALGHI DCTYGADAMY APSRKWLAGP RGVGVLAVNP VLEYLLPQWA GHVEAHVAGW  240
VGLSVAVGQH LAAGPERIQG ALAERGRAAR KILGELKDWR VIESVDEPSA ITTLEPVGDI  300
DVIAVRARLI EEHAIVTTGA ETIRAPFEMT TPVLRVSPHV DGTDEELELL AGALASARRV  360

SEQ ID NO: 11           moltype = DNA  length = 19
FEATURE                 Location/Qualifiers
misc_feature            1..19
```

-continued

```
                         note = Sequence of primer for synthesis of the optimized
                          EgtA gene
source                   1..19
                         mol_type = other DNA
                         organism = synthetic construct
SEQUENCE: 11
ggttcgtaac aaggatggt                                                        19

SEQ ID NO: 12           moltype = DNA  length = 21
FEATURE                 Location/Qualifiers
misc_feature            1..21
                        note = Sequence of primer for synthesis of the optimized
                         EgtA gene
source                  1..21
                        mol_type = other DNA
                        organism = synthetic construct
SEQUENCE: 12
aacaaggtag tcagatggta g                                                     21

SEQ ID NO: 13           moltype = DNA  length = 18
FEATURE                 Location/Qualifiers
misc_feature            1..18
                        note = Sequence of primer for synthesis of the optimized
                         EgtB gene
source                  1..18
                        mol_type = other DNA
                        organism = synthetic construct
SEQUENCE: 13
tctgtgctgg ttcctgag                                                         18

SEQ ID NO: 14           moltype = DNA  length = 18
FEATURE                 Location/Qualifiers
misc_feature            1..18
                        note = Sequence of primer for synthesis of the optimized
                         EgtB gene
source                  1..18
                        mol_type = other DNA
                        organism = synthetic construct
SEQUENCE: 14
ttcctgacga cggtatcc                                                         18

SEQ ID NO: 15           moltype = DNA  length = 18
FEATURE                 Location/Qualifiers
misc_feature            1..18
                        note = Sequence of primer for synthesis of the optimized
                         EgtC gene
source                  1..18
                        mol_type = other DNA
                        organism = synthetic construct
SEQUENCE: 15
ctcgtcgtcc agtcatac                                                         18

SEQ ID NO: 16           moltype = DNA  length = 18
FEATURE                 Location/Qualifiers
misc_feature            1..18
                        note = Sequence of primer for synthesis of the optimized
                         EgtC gene
source                  1..18
                        mol_type = other DNA
                        organism = synthetic construct
SEQUENCE: 16
cagcagcaac aacacatc                                                         18

SEQ ID NO: 17           moltype = DNA  length = 19
FEATURE                 Location/Qualifiers
misc_feature            1..19
                        note = Sequence of primer for synthesis of the optimized
                         EgtD gene
source                  1..19
                        mol_type = other DNA
                        organism = synthetic construct
SEQUENCE: 17
cgttggaatg gtgatgaag                                                        19

SEQ ID NO: 18           moltype = DNA  length = 18
FEATURE                 Location/Qualifiers
misc_feature            1..18
                        note = Sequence of primer for synthesis of the optimized
                         EgtD gene
```

-continued

```
source              1..18
                    mol_type = other DNA
                    organism = synthetic construct
SEQUENCE: 18
caagtgacag tccgaagt                                              18

SEQ ID NO: 19       moltype = DNA   length = 18
FEATURE             Location/Qualifiers
misc_feature        1..18
                    note = Sequence of primer for synthesis of the optimized
                     EgtE gene
source              1..18
                    mol_type = other DNA
                    organism = synthetic construct
SEQUENCE: 19
ctgccatcac cactcttg                                              18

SEQ ID NO: 20       moltype = DNA   length = 19
FEATURE             Location/Qualifiers
misc_feature        1..19
                    note = Sequence of primer for synthesis of the optimized
                     EgtE gene
source              1..19
                    mol_type = other DNA
                    organism = synthetic construct
SEQUENCE: 20
gctcctcatc agttccatc                                             19
```

GENE RELATED TO BIOSYNTHESIS OF ERGOTHIONEINE, AND USE THEREOF

CROSS-REFERENCE TO RELATED APPLICATION

This patent application claims the benefit and priority of Chinese Patent Application No. 202311036218.8 filed with the China National Intellectual Property Administration on Aug. 17, 2023, the disclosure of which is incorporated by reference herein in its entirety as part of the present application.

REFERENCE TO SEQUENCE LISTING

A computer readable XML file entitled "GWP20240402692_SequenceListing" is filed with this application. The computer readable XML file was created on May 20, 2024, with a file size of about 33,771 bytes, contains the sequence listing for this application, and is hereby incorporated by reference in its entirety.

TECHNICAL FIELD

The present disclosure belongs to the technical field of genetic engineering and particularly relates to a sequence of a gene related to synthesis of ergothioneine, and use of the sequence in construction of transgenic rice.

BACKGROUND

Ergothioneine, a type of natural amino acid synthesized only by fungi, is highly protective of cells and can protect DNAs and proteins from oxidative damage, thus being a natural and non-toxic antioxidant. In biochemical reactions at the cellular level, ergothioneine is 6,000 times more effective than vitamin E in protecting DNA. Among many antioxidants, ergothioneine can chelate heavy metal ions to protect red blood cells in the body from free radical damages, and can also synergistically stabilize vitamins and derivatives thereof, astaxanthin, ectoin, retinol and other substances to jointly protect cells from the free radical damages. In addition to free radical scavengers, ergothioneine is also a unique physiological protective agent with various physiological functions such as anti-aging, anti-radiation, and maintenance of DNA synthesis and normal cell growth. 1.5% ergothioneine can almost completely scavenge reactive oxygen species (ROS) free radicals induced by ultraviolet (UV) light, and its free radical scavenging capacity is 14 times that of glutathione and 30 times that of coenzyme Q10 at the same concentration. At present, ergothioneine is widely used in the cosmetics industry as a safe additive, including many cosmetics such as facial creams, eye creams, skin care essences, sunscreens, and lotions.

The traditional method of extracting ergothioneine from fungal fruiting bodies is plagued by problems such as low extract content, impurities and pesticide residues. Chemical synthesis easily produces toxic impurities and cannot guarantee product safety. Microbial fermentation has suffered from low fermentation efficiency, many impurities, and high difficulty in purification. Compared with microorganisms and animal reaction systems, rice seeds exhibit easy extraction and processing as well as low production cost as a molecular farm for expressing complex proteins. At the same time, since rice seeds do not contain alkaloids or allergens that are harmful to human body, rice is an excellent substrate for the production of ergothioneine. However, there have been no reports on the production of ergothioneine from rice seeds due to the lack of synthesis pathway for ergothioneine in rice.

SUMMARY

An objective of the present disclosure is to provide a gene related to biosynthesis of ergothioneine and a method for producing the ergothioneine using rice seeds.

To achieve the above objective, the present disclosure provides the following technical solutions:

The present disclosure provides a gene related to biosynthesis of ergothioneine, where the gene is one or more selected from the group consisting of an EgtA gene, an EgtB gene, an EgtC gene, an EgtD gene, and an EgtE gene;

the EgtA gene has the nucleotide sequence set forth in SEQ ID NO: 1;

the EgtB gene has the nucleotide sequence set forth in SEQ ID NO: 2;

the EgtC gene has the nucleotide sequence set forth in SEQ ID NO: 3;

the EgtD gene has the nucleotide sequence set forth in SEQ ID NO: 4; and the EgtE gene has the nucleotide sequence set forth in SEQ ID NO: 5.

Further, the gene includes sequences that are highly homologous to the EgtA gene, the EgtB gene, the EgtC gene, the EgtD gene, and the EgtE gene and encode the same proteins of the EgtA gene, the EgtB gene, the EgtC gene, the EgtD gene, and the EgtE gene, respectively;

the protein encoded by the EgtA gene has the amino acid sequence set forth in SEQ ID NO: 6;

the protein encoded by the EgtB gene has the amino acid sequence set forth in SEQ ID NO: 7;

the protein encoded by the EgtC gene has the amino acid sequence set forth in SEQ ID NO: 8;

the protein encoded by the EgtD gene has the amino acid sequence set forth in SEQ ID NO: 9; and the protein encoded by the EgtE gene has the amino acid sequence set forth in SEQ ID NO: 10.

The present disclosure further provides a gene expression unit, including the gene and an endosperm-specific rice globulin-1 promoter and a terminator.

The present disclosure further provides a vector, including one or more of the genes, or the gene expression unit.

Preferably, the five gene expression units in the vector are presented as a tandem sequence.

More preferably, the tandem sequence is an EgtA-containing expression unit-EgtB-containing expression unit-EgtC-containing expression unit-EgtD-containing expression unit-EgtE-containing expression unit.

The present disclosure further provides a method for constructing the vector, including sequentially cloning the gene expression units into a plant expression vector to obtain a recombinant plasmid vector.

The present disclosure further provides a host bacterium including the vector.

The present disclosure further provides the use of the EgtA gene, the EgtB gene, the EgtC gene, the EgtD gene, and the EgtE gene, or the gene expression unit, the vector, or the host bacterium that includes the genes in biosynthesis of ergothioneine.

The present disclosure further provides a method for biosynthesis of ergothioneine, including: transforming rice with the vector including one or more of the EgtA gene, the EgtB gene, the EgtC gene, the EgtD gene, and the EgtE gene to obtain a rice plant capable of biosynthesizing ergothioneine, and then isolating the ergothioneine from a rice seed on the rice plant.

The present disclosure has the following beneficial effects:

(1) In the present disclosure, nucleic acid sequences suitable for rice expression system are obtained by optimizing five ergothioneine synthesis genes in *Mycobacteroides abscessus* and can be stably inherited and expressed efficiently in rice.

(2) In the present disclosure, the five genes related to ergothioneine synthesis are optimized and synthesized, ligated to a rice endosperm-specific expression promoter, and then expressed in the rice endosperm in a tandem manner, thus obtaining an engineered rice plant capable of synthesizing ergothioneine. The gene shows an application potential in fields such as the production of ergothioneine in rice molecular farms.

(3) In the present disclosure, the rice as a molecular farm does not contain alkaloids or allergens that are harmful to human body, and the biosynthesized ergothioneine exhibits easy extraction and processing as well as low production cost.

DETAILED DESCRIPTION OF THE EMBODIMENTS

Figure 1:
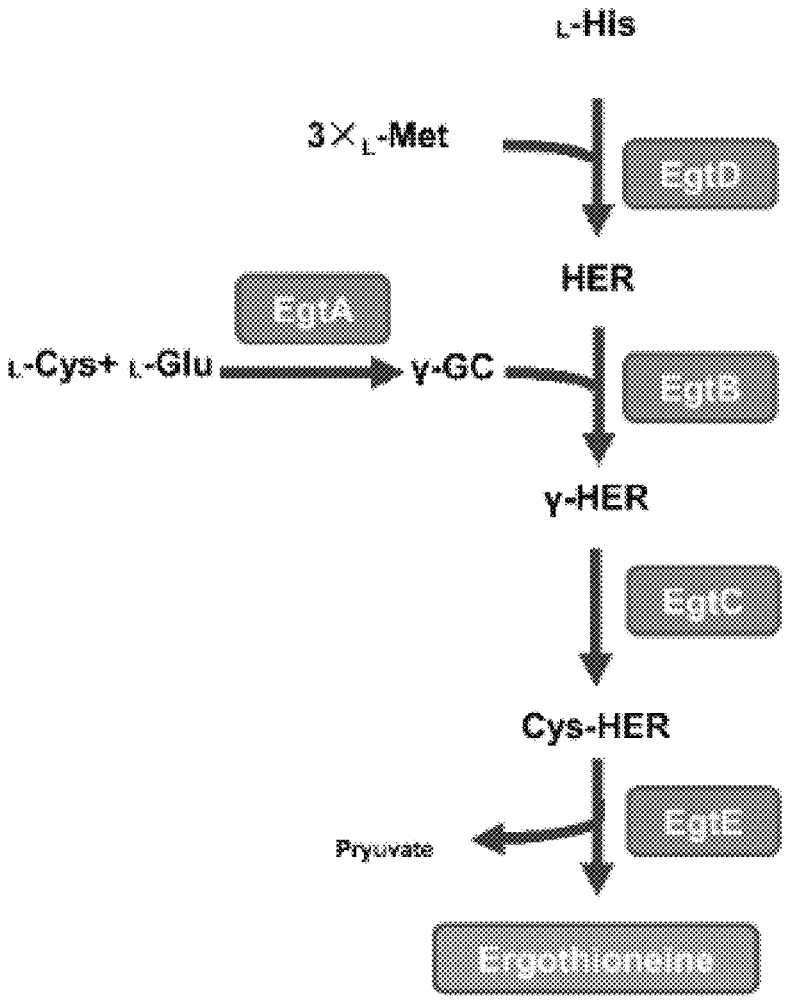
FIG. 1 shows a schematic diagram of a synthetic pathway designed in the present disclosure for synthesizing ergothioneine from rice endosperm.

Based on five synthesis genes of ergothioneine in *Mycobacteroides abscessus*, only an encoding sequence of each of the five genes is retained, and a gene structure of an encoding region in each gene is optimized following the principles below:

(I) The gene codons are optimized to improve gene translation efficiency.

(II) The recognition sites of commonly used restriction endonucleases within the gene are eliminated to facilitate the construction of expression cassettes.

(III) The inverted repeat sequences, stem-loop structures, and transcription termination signals are eliminated to balance GC/AT within the gene and improve RNA stability.

(IV) The gene-encoded protein is made in conformity to the N-terminal principle to improve the stability of the translated protein.

(V) The free energy of mRNA secondary structure is optimized to improve gene expression efficiency. The optimized nucleotide sequences of the five genes related to the synthesis of ergothioneine are as follows:

the EgtA gene has the nucleotide sequence set forth in SEQ ID NO: 1;

the EgtB gene has the nucleotide sequence set forth in SEQ ID NO: 2;

the EgtC gene has the nucleotide sequence set forth in SEQ ID NO: 3;

the EgtD gene has the nucleotide sequence set forth in SEQ ID NO: 4; and the EgtE gene has the nucleotide sequence set forth in SEQ ID NO: 5.

The gene further includes sequences that are highly homologous to the EgtA gene, the EgtB gene, the EgtC gene, the EgtD gene, and the EgtE gene and encode same proteins of the EgtA gene, the EgtB gene, the EgtC gene, the EgtD gene, and the EgtE gene, respectively;

the protein encoded by the EgtA gene has the amino acid sequence set forth in SEQ ID NO: 6;

the protein encoded by the EgtB gene has the amino acid sequence set forth in SEQ ID NO: 7;

the protein encoded by the EgtC gene has the amino acid sequence set forth in SEQ ID NO: 8;

the protein encoded by the EgtD gene has the amino acid sequence set forth in SEQ ID NO: 9; and the protein encoded by the EgtE gene has the amino acid sequence set forth in SEQ ID NO: 10.

The "highly homologous" refers to a sequence similarity of not less than 95%.

The present disclosure further provides a gene expression unit, including the gene and an endosperm-specific rice globulin-1 promoter and a terminator.

Preferably, an endosperm-specific rice globulin-1 promoter and a terminator are ligated to both ends of each gene to form a gene expression unit.

More preferably, two ends of the expression unit are ligated with restriction sites, including Sac I, Xho I, BamH I, Sal I, Hind III, and EcoR I restriction sites.

Most preferably, two ends of the expression unit containing EgtA are ligated to the Sac I and Xho I restriction sites;

two ends of the expression unit containing EgtB are ligated to the Xho I and BamH I restriction sites;

two ends of the expression unit containing EgtC are ligated to the BamH I and Sal I restriction sites;

two ends of the expression unit containing EgtD are ligated to the Sac I and Hind III restriction sites; and two ends of the expression unit containing EgtE are ligated to the Hind III and EcoR I restriction sites.

The present disclosure further provides a vector, including one or more of the EgtA gene, the EgtB, the EgtC, the EgtD, and the EgtE gene, or the gene expression unit.

Preferably, the gene expression units containing the EgtA gene, the EgtB gene, the EgtC gene, the EgtD gene, and the EgtE gene in the vector are presented as a tandem sequence; and most preferably, the tandem sequence is an EgtA-containing expression unit-EgtB-containing expression unit-EgtC-containing expression unit-EgtD-containing expression unit-EgtE-containing expression unit.

The present disclosure further provides a method for constructing the vector, including sequentially cloning the gene expression units into a plant expression vector to obtain a recombinant plasmid vector.

Optionally, the plant expression vector uses a pCamBIA series expression vector.

Preferably, the plant expression vector uses pCamBIA-1301 or a plant binary vector pYP694 that is obtained by using pCamBIA-1301 as a backbone and modifying the backbone by introducing a new multiple cloning site.

The plant binary vector pYP694 is from the Shanghai Academy of Agricultural Sciences, Tian Y S et al. Enhancing carotenoid biosynthesis in rice endosperm by metabolic engineering. *Plant Biotechnol J.* 2019 May; 17(5): 849-851.

The present disclosure further provides a host bacterium including the vector; optionally, the host bacterium is *Agrobacterium* EHA105.

The present disclosure further provides the use of the gene in biosynthesis of ergothioneine by rice.

The present disclosure further provides a method for biosynthesis of ergothioneine, including: transforming rice with the vector to obtain a rice plant capable of biosynthesizing ergothioneine, and then isolating the ergothioneine from a rice seed on the rice plant.

In the present disclosure, unless otherwise specified, all raw material components are commercially available products well known to persons skilled in the art. All experiments involving molecular biology are referred to the book "Molecular Cloning" (written by J. Sambrook, E. Fritsch, and T. Maniatis, 1994, Science Press) unless otherwise noted. The rice seeds (Nipponbare) used are preserved by the Agricultural Synthetic Biology Research Center of the Institute of Biotechnology, Shanghai Academy of Agricultural Sciences. Unless otherwise specified, the reagents used are purchased from Sangon Biotech (Shanghai) Co., Ltd. or Shanghai Sinopharm Group Co., Ltd.

The technical solutions in the present disclosure are clearly and completely described below with reference to the examples of the present disclosure. Apparently, the described examples are merely a part rather than all of the examples of the present disclosure. All other embodiments obtained by those skilled in the art based on the embodiments of the present disclosure without creative efforts shall fall within the protection scope of the present disclosure.

Example 1

Optimization and Synthesis of Five Genes Required for the Synthesis of Ergothioneine in Rice Endosperm In the present disclosure, an ergothioneine synthesis pathway suitable for rice chassis was first designed (FIG. 1), and then an endosperm-specific rice globulin-1 promoter and a terminator were ligated to both ends of each gene (the EgtA, the EgtB, the EgtC, the EgtD, and the EgtE gene) to form a gene expression unit. Restriction sites were ligated at both ends of the gene expression unit, where Sac I and Xho I restriction sites were ligated at both ends of the EgtA-containing expression unit; Xho I and BamH I restriction sites were ligated at both ends of the EgtB-containing expression unit; BamH I and Sal I restriction sites were ligated at both ends of the EgtC-containing expression unit; Sac I and Hind III restriction sites were ligated at both ends of the EgtD-containing expression unit; Hind III and EcoR I restriction sites were ligated at both ends of the EgtE-containing expression unit. The full-length sequence was synthesized by Sangon Biotech (Shanghai) Co., Ltd.

Example 2

Construction of pYB4087 Rice-Specific Expression Vector

A plant binary vector pYP694 was selected as an initial vector backbone to construct a rice-specific expression vector. The plant binary vector pYP694 was from the Shanghai Academy of Agricultural Sciences, Tian Y S et al. Enhancing carotenoid biosynthesis in rice endosperm by metabolic engineering. *Plant Biotechnol J.* 2019 May; 17(5): 849-851.

The EgtA-containing expression unit in Example 1 was integrated into the pYP694 vector through Sac I and Xho I restriction enzymes to generate a construct pYP694-GEgtA;

the EgtB-containing expression unit in Example 1 was integrated into the pYP694-GEgtA vector through Xho I and BamH I restriction enzymes to generate a two-gene construct pYP694-GEgtA-EgtB;

the EgtC-containing expression unit in Example 1 was integrated into the pYP694-GEgtA-EgtB vector through BamH I and Sal I restriction enzymes to generate a three-gene construct pYP694-GEgtA-EgtB-EgtC;

the EgtD-containing expression unit in Example 1 was integrated into the pYP694-GEgtA-EgtB-EgtC vector through Sal I and Hind III restriction enzymes to generate a four-gene construct pYP694-GEgtA-EgtB-EgtC-EgtD; and the EgtE-containing expression unit in Example 1 was integrated into the pYP694-GEgtA-EgtB-EgtC-EgtD vector through Hind III and EcoR I restriction enzymes to generate a five-gene construct pYP694-GEgtA-EgtB-EgtC-EgtD-EgtE.

Figure 2:
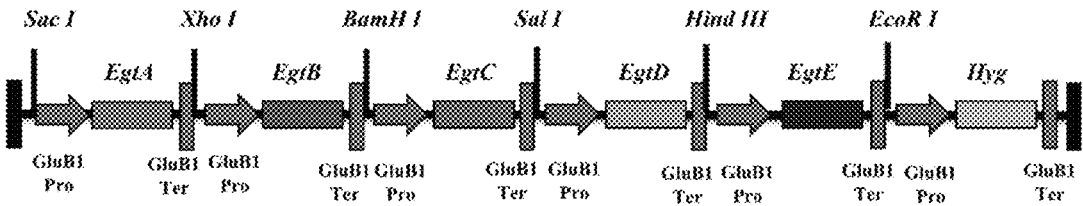
FIG. 2 shows a schematic diagram of construction of vector for synthesizing ergothioneine from rice endosperm.

The construct pYB4087 containing five genes was successfully obtained (FIG. 2).

Example 3

*Agrobacterium*-Mediated Transformation of Rice

1) Preparation of *Agrobacterium*

The pYB4087 vector containing the target gene in Example 2 was transformed into *Agrobacterium* EHA105 by electroporation. The target *Agrobacterium* was re-cultivated to a concentration of $OD_{600}$=0.3-0.5, and an *Agrobacterium* suspension was prepared for co-cultivation and transformation of rice.

2) Genetic Transformation of Rice

Figure 3:
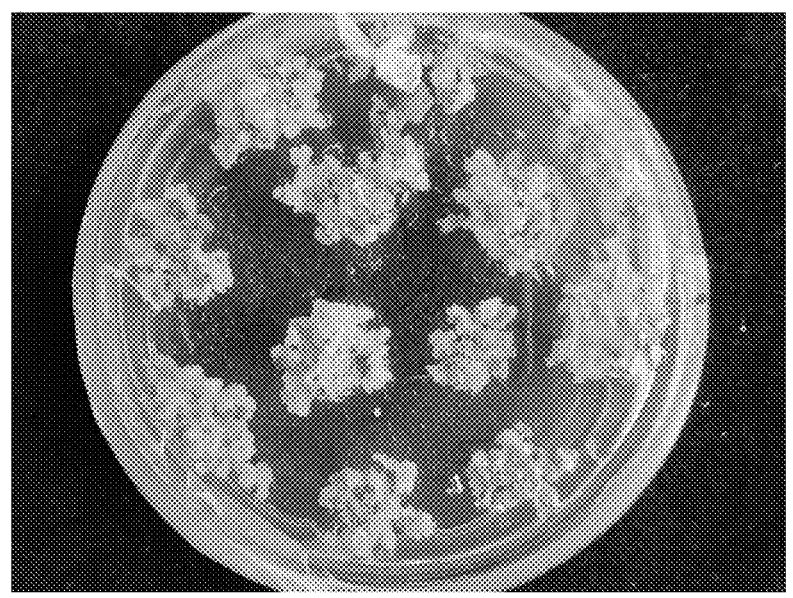
FIG. 3 shows the induction of rice callus.
Figure 4:
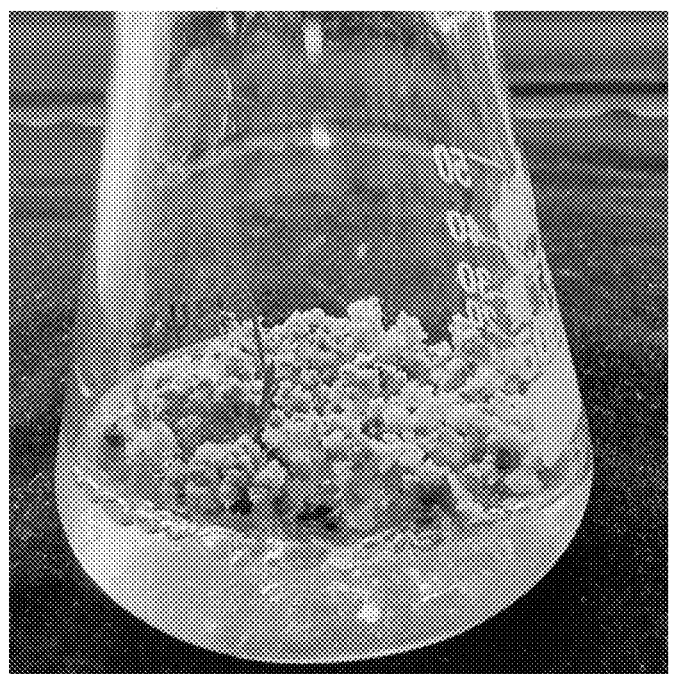
FIG. 4 shows the differentiated seedlings obtained from rice differentiation.

Rice seeds were sterilized with 0.1% mercury and then subcultured on an induction medium to produce callus with light yellow color (FIG. 3). The callus was co-cultured with *Agrobacterium* for 2-3 days, then placed on a screening medium and cultured in the dark for 14 days, and then placed in a differentiation medium to differentiate to obtain rice seedlings (FIG. 4), which were subjected to rooting, seedling strengthening, and transplanting to obtain mature rice.

Example 4

Detection of Transgenic Positive Plants

DNA was extracted from the rice cultured in Example 3 and the expression of each gene was detected according to the following PCR reaction system:

10×PCR buffer 5.0 μL; dNTPs 4 μL (2.5 mmol/L); template 1 μL (20 ng to 50 ng); primer Z 1 μL; primer F 1 μL; Taq enzyme 0.2 μL; diluted with sterile water to a volume of 50 μL.

The PCR primers corresponding to the five genes are shown in Table 1.

7

TABLE 1

PCR primers

| Gene | Primer Z | Primer F |
|---|---|---|
| EgtA | GGTTCGTAACAAGGATGGT (SEQ ID NO: 11) | AACAAGGTAGTCAGATGGTAG (SEQ ID NO: 12) |
| EgtB | TCTGTGCTGGTTCCTGAG (SEQ ID NO: 13) | TTCCTGACGACGGTATCC (SEQ ID NO: 14) |
| EgtC | CTCGTCGTCCAGTCATAC (SEQ ID NO: 15) | CAGCAGCAACAACACATC (SEQ ID NO: 16) |
| EgtD | CGTTGGAATGGTGATGAAG (SEQ ID NO: 17) | CAAGTGACAGTCCGAAGT (SEQ ID NO: 18) |
| EgtE | CTGCCATCACCACTCTTG (SEQ ID NO: 19) | GCTCCTCATCAGTTCCATC (SEQ ID NO: 20) |

Figure 5:
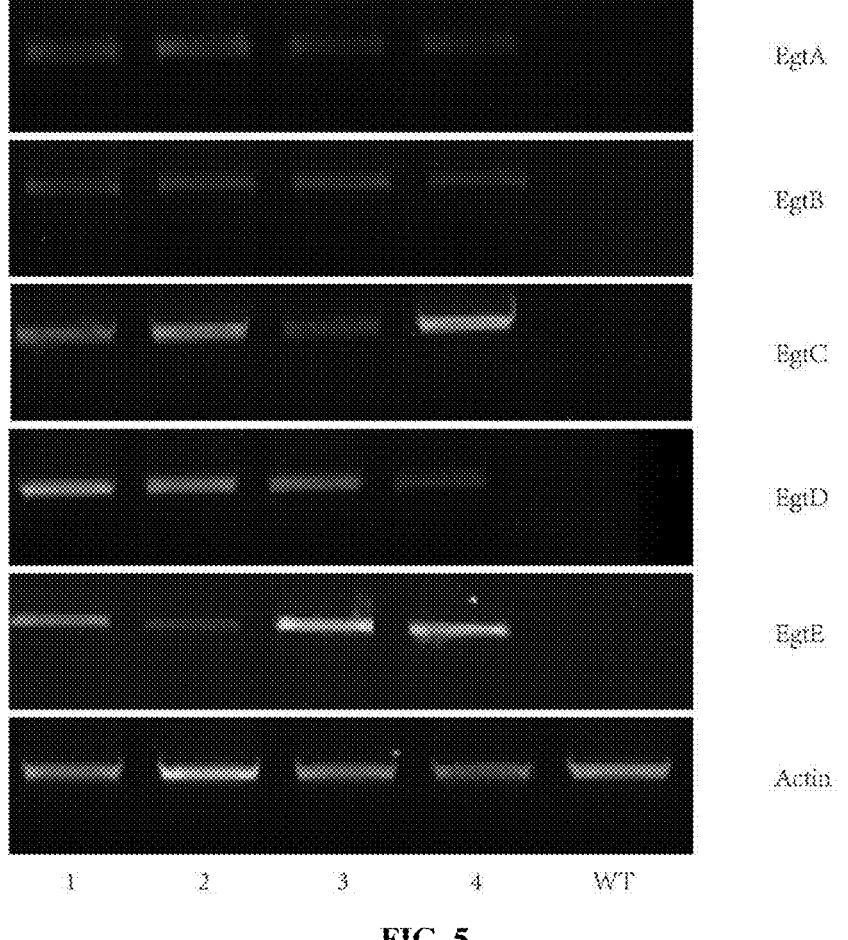
FIG. 5 shows the expression of genes related to biosynthesis of ergothioneine in different engineered rice lines detected by RT-PCR.

The reaction program included: 94° C. for 5 min; 94° C. for 20 s, 56° C. for 30 s, 72° C. for 30 s; 72° C. for 10 min; 32 cycles. The detection results are shown in FIG. 5.

Example 5

Construction of a Rice Molecular Farm for the Production of Ergothioneine

The rice plants that tested positive in Example 4 were planted into farmland according to the following steps:

1) The suitable land was selected to allow plowing, fertilization, irrigation and the like to ensure that the soil fertility and moisture met the needs of rice growth.

2) The selected rice seeds were sown in the field. Sowing methods included direct seeding and field planting. The direct seeding was to sow the seeds directly in the field; while the field planting was to plant the seedlings in the field and then transplant same to the field after the seedlings grew to a certain height.

3) After sowing, the fields needed to be regularly managed, including weeding, irrigation, fertilization, and pest and disease control.

4) The rice was harvested after maturing. The harvesting included manual harvesting and machine harvesting.

Figure 6:
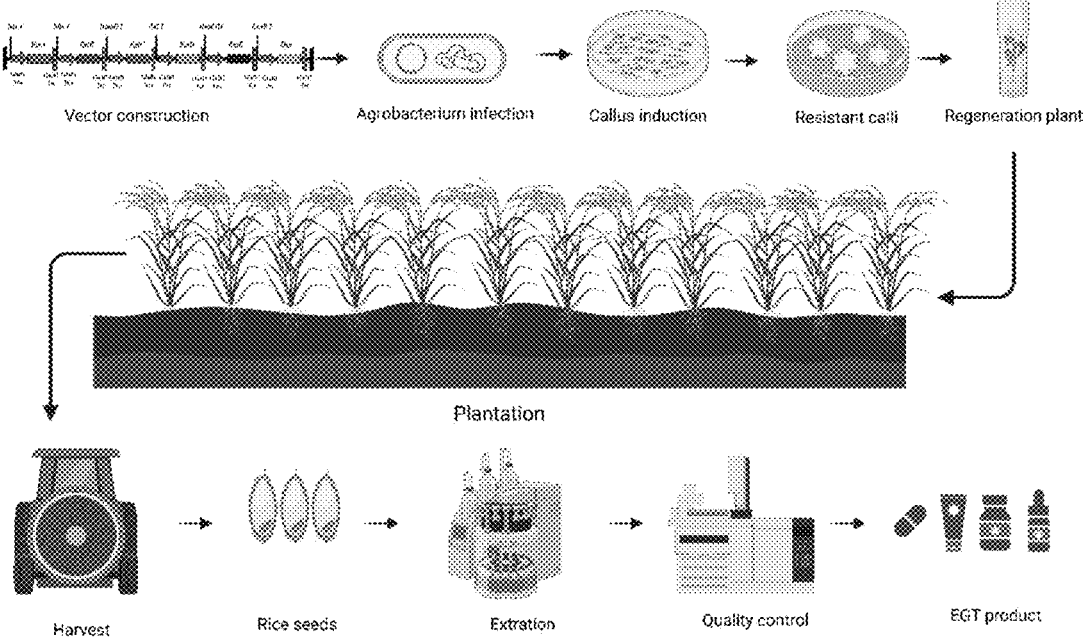
FIG. 6 shows a schematic flow chart for producing ergothioneine in a rice molecular farm.

5) After harvesting, the rice needed to be threshed: the rice was separated from the husk for easy storage and extraction (FIG. 6).

Example 6

UPLC-MS/MS Targeted Metabolomics Detection of Ergothioneine Content

After the rice in Example 5 was grown for 60 days, the UPLC-MS/MS targeted metabolomics was conducted to detect the ergothioneine content, specifically including:

1) Metabolite Extraction

A sample was thawed in a refrigerator at 4° C., vortexed for 2 min, and 1 mL of the sample was transferred into an EP tube and centrifuged at 8,000 rpm for 10 min at 4° C. The supernatant was then removed to retain a precipitate, and 100 μL of pre-cooled 80% methanol was added into the EP tube containing the precipitate, vortexed for 1 min, sonicated in ice water for 5 min, and then centrifuged at 13,000 rpm at 4° C. for 15 min. 80 μL of the resulting supernatant was collected into an injection vial.

This project used an ultra-high performance liquid chromatograph to conduct chromatographic separation of target compounds through a liquid chromatography column. The liquid chromatograph was Waters Acquity I class UPLC. The mass spectrometer was Waters XEVO TQD. The chromatographic column was Waters Acquity UPLC R BEH C18 (2.1 mm×100 mm, 1.7 μm). The centrifuge was Thermo Scientific Heraeus Fresco17 centrifuge. The vortex meter was VXMAL OHAUS Germany. The balance was BSA124S-CW Sartorius Germany. The ultrasound machine was SB-3200 DT Ningbo Xinzhi, China. Methanol was of LC-MS grade, purchased from Thermo fisher (Thermo fisher scientific Inc, MA USA), acetonitrile was of LC-MS grade, purchased from Thermo fisher (Thermo fisher scientific Inc, MA USA). Formic acid was of LC-MS grade, purchased from Shanghai Aladdin Biochemical Technology Co., Ltd., China. Ultrapure water was Watsons purified water.

2) The Parameters Were as Follows

| | |
|---|---|
| Mobile phase A | Water + 0.1% formic acid |
| Mobile phase B | ACN + 0.1% formic acid |
| Column temperature/° C. | 35 |
| Sample vial rack temperature/° C. | 8 |
| Injection volume/μL | 5 |

The liquid phase gradient was:

| Time/min | Flow rate mL/min | B % |
|---|---|---|
| 0 | 0.3 | 10 |
| 0.2 | 0.3 | 10 |
| 1.0 | 0.3 | 80 |
| 1.2 | 0.3 | 80 |
| 1.5 | 0.3 | 10 |
| 2.0 | 0.3 | 10 |

3) MS Parameters

This project used a Waters triple quadrupole mass spectrometer equipped with an ESI ion source to conduct mass spectrometry analysis in dynamic multiple reaction monitoring (MRM) mode. The ion source parameters were as follows:

| Ion source mode | ESI+ |
|---|---|
| Capillary voltage/kV | 3.7 |
| Ion source temperature/° C. | 150 |
| Desolvation gas temperature/° C. | 400 |
| Desolvation gas flow rate/(L/hour) | 800 |
| Cone gas flow rate/(L/hour) | 20 |

The MRM channels were as follows:

| Compound name | Parent ion (m/z) | Daughter ion (m/z) | Cone voltage (V) | Collision energy (V) |
|---|---|---|---|---|
| ET* | 230.1 | 186.0000 | 30 | 10 |
| ET | 230.1 | 127.0008 | 50 | 20 |

Figure 7:
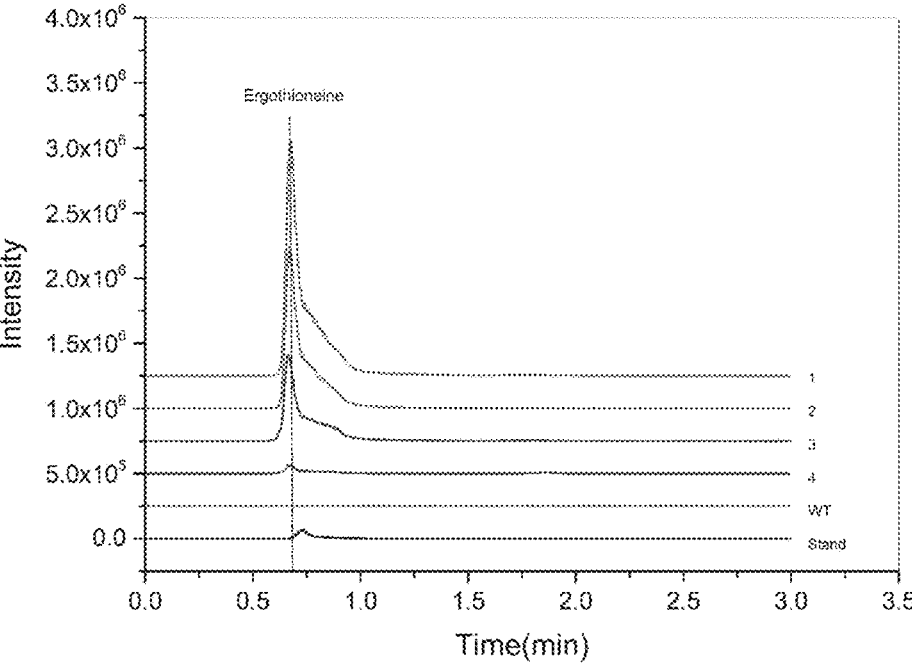
FIG. 7 shows an ergothioneine content in the rice endosperm detected using UPLC-MS/MS targeted metabolomics.

The results showed that ergothioneine accumulation could be detected in the engineered rice seeds, while there was no ergothioneine in the wild-type rice seeds (FIG. 7).

Example 7

Detection of Ergothioneine Production

Figure 8:
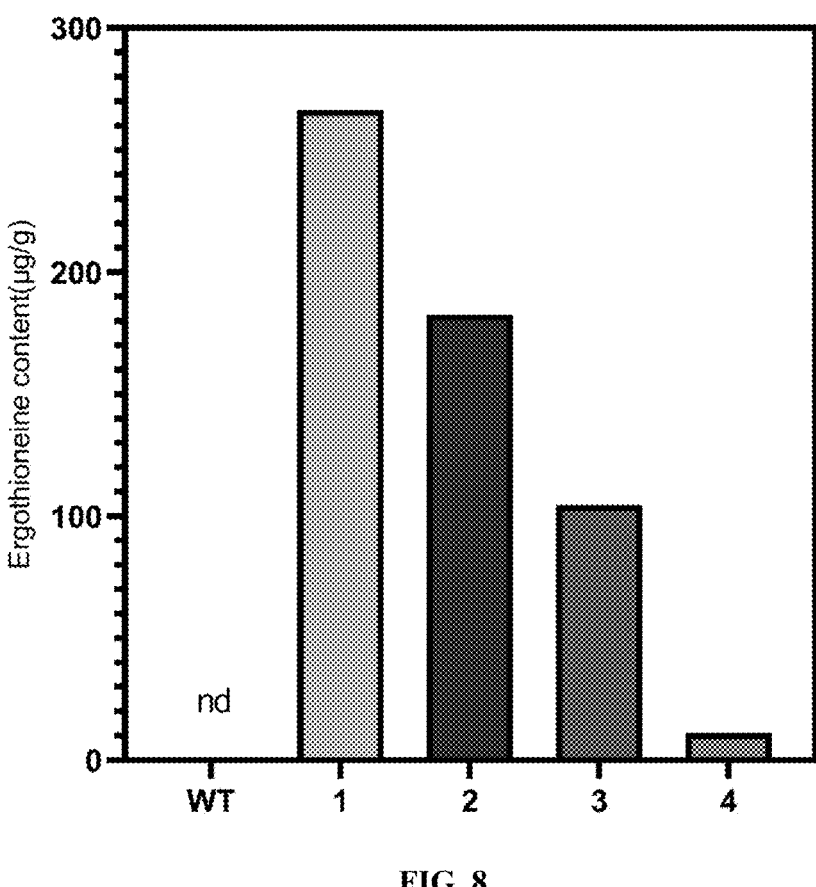
FIG. 8 shows the ergothioneine contents in different rice lines in Example 7, where a rice line numbered 1 has a yield of up to 266 µg/g.

Methanol was used to prepare an ergothioneine standard, and a calibration solution was analyzed by UPLC-MS/MS using the method in Example 6. y represented the peak area of the target compound, and x represented the concentration of the target compound (ng/ml). Linear regression was conducted using a least squares method. When the weight was set to "NULL", the recovery rate (accuracy) and linear coefficient ($R^2$) of the calibration solution were the best and both R and $R^2$ were greater than 0.99. If a signal-to-noise ratio (S/N) of a certain calibration concentration was approximately to or less than 10, the calibration point for that concentration should be excluded. The final calibration curve included a minimum of 5 calibration points. The ergothioneine production in the rice seeds of different rice lines in Example 6 was detected, and the results are shown in FIG. 8. It was seen that the ergothioneine production in the genetically engineered rice constructed by the present disclosure could reach 266 µg/g.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

---

What is claimed is:

1. A gene related to biosynthesis of ergothioneine, wherein the gene is one or more selected from the group consisting of an EgtA gene, an EgtB gene, an EgtC gene, an EgtD gene, and an EgtE gene; wherein:

the EgtA gene has the nucleotide sequence set forth in SEQ ID NO: 1 or a nucleotide sequence having at least 95% sequence identity to SEQ ID NO: 1;

the EgtB gene has the nucleotide sequence set forth in SEQ ID NO: 2 or a nucleotide sequence having at least 95% sequence identity to SEQ ID NO: 2;

the EgtC gene has the nucleotide sequence set forth in SEQ ID NO: 3 or a nucleotide sequence having at least 95% sequence identity to SEQ ID NO: 3;

the EgtD gene has the nucleotide sequence set forth in SEQ ID NO: 4 or a nucleotide sequence having at least 95% sequence identity to SEQ ID NO: 4; and the EgtE gene has the nucleotide sequence set forth in SEQ ID NO: 5 or a nucleotide sequence having at least 95% sequence identity to SEQ ID NO: 5.

2. The gene according to claim 1, wherein:

the EgtA gene encodes a protein having the amino acid sequence set forth in SEQ ID NO: 6;

the EgtB gene encodes a protein having the amino acid sequence set forth in SEQ ID NO: 7;

the EgtC gene encodes a protein having the amino acid sequence set forth in SEQ ID NO: 8;

the EgtD gene encodes a protein having the amino acid sequence set forth in SEQ ID NO: 9; and the EgtE gene encodes a protein having the amino acid sequence set forth in SEQ ID NO: 10.

3. A gene expression unit, comprising the gene according to claim 1 and an endosperm-specific rice globulin-1 promoter and a terminator.

4. The gene expression unit according to claim 3, wherein:

the EgtA gene encodes a protein having the amino acid sequence set forth in SEQ ID NO: 6;

the EgtB gene encodes a protein having the amino acid sequence set forth in SEQ ID NO: 7;

the EgtC gene encodes a protein having the amino acid sequence set forth in SEQ ID NO: 8;

the EgtD gene encodes a protein having the amino acid sequence set forth in SEQ ID NO: 9; and the EgtE gene encodes a protein having the amino acid sequence set forth in SEQ ID NO: 10.

5. A vector, comprising one or more of the genes according to claim 1 or a gene expression unit.

6. The vector according to claim 5, wherein the gene expression unit is present in a form of a tandem sequence.

7. The vector according to claim 5, wherein:

the EgtA gene encodes a protein having the amino acid sequence set forth in SEQ ID NO: 6;

the EgtB gene encodes a protein having the amino acid sequence set forth in SEQ ID NO: 7;

the EgtC gene encodes a protein having the amino acid sequence set forth in SEQ ID NO: 8;

the EgtD gene encodes a protein having the amino acid sequence set forth in SEQ ID NO: 9; and the EgtE gene encodes a protein having the amino acid sequence set forth in SEQ ID NO: 10.

8. The vector according to claim 6, wherein the tandem sequence is an EgtA-containing expression unit—EgtB-containing expression unit—EgtC-containing expression unit—EgtD-containing expression unit—EgtE-containing expression unit.

9. A method for constructing the vector according to claim 8, comprising sequentially cloning the gene expression units into a plant expression vector to obtain a recombinant plasmid vector.

10. A host bacterium comprising the vector according to claim 5.

11. The host according to claim 10, wherein the vector comprises a gene expression unit or one or more of the genes selected from the group consisting of an EgtA gene, an EgtB gene, an EgtC gene, an EgtD gene, and an EgtE gene; wherein:

the EgtA gene has the nucleotide sequence set forth in SEQ ID NO: 1;

the EgtB gene has the nucleotide sequence set forth in SEQ ID NO: 2;

the EgtC gene has the nucleotide sequence set forth in SEQ ID NO: 3;

the EgtD gene has the nucleotide sequence set forth in SEQ ID NO: 4; and the EgtE gene has the nucleotide sequence set forth in SEQ ID NO: 5.

12. The vector according to claim 11, wherein the gene expression unit is present in a form of a tandem sequence.

13. The vector according to claim 11, wherein:

the EgtA gene encodes a protein having the amino acid sequence set forth in SEQ ID NO: 6;

the EgtB gene encodes a protein having the amino acid sequence set forth in SEQ ID NO: 7;

the EgtC gene encodes a protein having the amino acid sequence set forth in SEQ ID NO: 8;

the EgtD gene encodes a protein having the amino acid sequence set forth in SEQ ID NO: 9; and the EgtE gene encodes a protein having the amino acid sequence set forth in SEQ ID NO: 10.

14. The vector according to claim 12, wherein the tandem sequence is an EgtA-containing expression unit—EgtB-containing expression unit—EgtC-containing expression unit—EgtD-containing expression unit—EgtE-containing expression unit.

15. A method for biosynthesis of ergothioneine, comprising: transforming rice with a vector to obtain a rice plant capable of biosynthesizing ergothioneine, and then isolating the ergothioneine from a rice seed on the rice plant; wherein the vector comprises one or more of the genes according to claim 1.

\* \* \* \* \*